(12) United States Patent
Shuman (10) Patent No.: US 11,602,286 B2
(45) Date of Patent: Mar. 14, 2023

(54) SIMULATED VALVE DEVICE FOR AIRWAY

(71) Applicant: Gyrus ACMI, Inc., Southborough, MA (US)

(72) Inventor: Brandon J. Shuman, Kirkland, WA (US)

(73) Assignee: GYRUS ACMI, INC., Westborough, MA (US)

( * ) Notice: Subject to any disclaimer, the term of this patent is extended or adjusted under 35 U.S.C. 154(b) by 96 days.

(21) Appl. No.: 15/300,408

(22) PCT Filed: Mar. 30, 2015

(86) PCT No.: PCT/US2015/023410
§ 371 (c)(1),
(2) Date: Sep. 29, 2016

(87) PCT Pub. No.: WO2015/153500
PCT Pub. Date: Oct. 8, 2015

(65) Prior Publication Data
US 2017/0181665 A1    Jun. 29, 2017

Related U.S. Application Data

(60) Provisional application No. 61/973,110, filed on Mar. 31, 2014, provisional application No. 61/973,142, (Continued)

(51) Int. Cl.
*A61B 5/107* (2006.01)
*A61B 1/012* (2006.01)
(Continued)

(52) U.S. Cl.
CPC ........ *A61B 5/1076* (2013.01); *A61B 1/00097* (2022.02); *A61B 1/012* (2013.01);
(Continued)

(58) Field of Classification Search
CPC ......... A61B 1/00; A61B 1/267; A61B 5/1076; A61M 25/04
See application file for complete search history.

(56) References Cited

U.S. PATENT DOCUMENTS 5,797,960 A * 8/1998 Stevens ............ A61B 17/00234
606/213
7,434,578 B2 * 10/2008 Dillard ............. A61B 17/12104
128/200.24
(Continued)

FOREIGN PATENT DOCUMENTS

WO   WO-2004006767 A2   1/2004
WO   WO-2013109398 A1   7/2013
(Continued)

OTHER PUBLICATIONS

"International Application Serial No. PCT/US2015/023410, International Preliminary Report on Patentability dated Oct. 13, 2016", 8 pgs.
(Continued)

*Primary Examiner* — Catherine B Kuhlman
*Assistant Examiner* — Raymond P Dulman
(74) *Attorney, Agent, or Firm* — Schwegman Lundberg & Woessner, P.A.

(57) ABSTRACT

Embodiments of a simulated valve device can be used to determine whether a valve device would fit within a particular airway. The simulated valve device can include a shaft having at least one strut extending radially therefrom. The strut and at least part of the shaft can be surrounded by a membrane for viewing through a bronchoscope. In some embodiments, the membrane can include markings for viewing by a user.

16 Claims, 5 Drawing Sheets

Related U.S. Application Data filed on Mar. 31, 2014, provisional application No. 61/973,137, filed on Mar. 31, 2014, provisional application No. 61/973,105, filed on Mar. 31, 2014, provisional application No. 61/973,169, filed on Mar. 31, 2014.

(51) Int. Cl.

| | | |
|---|---|---|
| *A61B 1/267* | (2006.01) | |
| *A61B 90/00* | (2016.01) | |
| *A61B 5/08* | (2006.01) | |
| *A61B 1/06* | (2006.01) | |
| *A61B 1/018* | (2006.01) | |
| *A61B 1/015* | (2006.01) | |
| *A61B 1/00* | (2006.01) | |
| *A61F 2/04* | (2013.01) | |
| *A61B 5/103* | (2006.01) | |
| *A61B 1/07* | (2006.01) | |
| *A61B 1/04* | (2006.01) | |

(52) U.S. Cl.
CPC .............. *A61B 1/015* (2013.01); *A61B 1/018* (2013.01); *A61B 1/0623* (2013.01); *A61B 1/0676* (2013.01); *A61B 1/0684* (2013.01); *A61B 1/267* (2013.01); *A61B 1/2676* (2013.01); *A61B 5/08* (2013.01); *A61B 5/1079* (2013.01); *A61B 90/06* (2016.02); *A61F 2/04* (2013.01); *A61B 1/04* (2013.01); *A61B 1/06* (2013.01); *A61B 1/0661* (2013.01); *A61B 1/07* (2013.01); *A61B 5/103* (2013.01); *A61B 5/107* (2013.01); *A61B 2090/061* (2016.02); *A61F 2002/043* (2013.01); *A61F 2220/0016* (2013.01)

(56) References Cited

U.S. PATENT DOCUMENTS

| | | | | |
|---|---|---|---|---|
| 7,691,151 | B2 * | 4/2010 | Kutsko | A61B 17/12022 128/200.24 |
| 7,909,803 | B2 * | 3/2011 | Tanaka | A61M 16/0833 604/275 |
| 7,942,931 | B2 * | 5/2011 | Gonzalez | A61B 17/12022 604/93.01 |
| 8,043,301 | B2 * | 10/2011 | Adams | A61F 2/2436 128/207.14 |
| 8,475,389 | B2 * | 7/2013 | Tanaka | A61M 1/04 600/538 |
| 8,518,053 | B2 * | 8/2013 | Tanaka | A61M 1/04 606/1 |
| 9,345,416 | B2 * | 5/2016 | MacAdam | A61B 5/6858 |
| 2003/0176886 | A1 * | 9/2003 | Wholey | A61F 2/013 606/200 |
| 2003/0216769 | A1 * | 11/2003 | Dillard | A61B 17/12104 606/191 |
| 2004/0060563 | A1 * | 4/2004 | Rapacki | A61B 17/12022 128/207.14 |
| 2005/0010138 | A1 * | 1/2005 | Mangiardi | A61B 5/103 600/587 |
| 2007/0106296 | A1 * | 5/2007 | Laufer | A61B 18/00 606/50 |
| 2007/0123851 | A1 * | 5/2007 | Alejandro | A61B 18/1492 606/45 |
| 2008/0072914 | A1 | 3/2008 | Hendricksen et al. | |
| 2009/0143705 | A1 * | 6/2009 | Danek | A61B 18/08 601/3 |
| 2009/0157043 | A1 * | 6/2009 | Leonard | A61M 31/00 604/509 |
| 2009/0287050 | A1 * | 11/2009 | Barthel | A61M 29/02 600/115 |
| 2010/0160832 | A1 * | 6/2010 | Braido | A61B 5/6884 600/587 |
| 2011/0023885 | A1 * | 2/2011 | Vazales | A61B 1/0669 128/207.14 |
| 2011/0098602 | A1 * | 4/2011 | Campbell | A61F 2/2496 600/587 |
| 2012/0053485 | A1 * | 3/2012 | Bloom | A61B 1/00082 600/567 |
| 2012/0184985 | A1 | 7/2012 | Ravenscroft et al. | |
| 2012/0209308 | A1 | 8/2012 | Kutsko et al. | |
| 2013/0253492 | A1 * | 9/2013 | Danek | A61B 18/08 606/21 |
| 2022/0022775 | A1 | 1/2022 | Johnson et al. | |

FOREIGN PATENT DOCUMENTS

| WO | WO-2015153500 A1 | 10/2015 |
|---|---|---|
| WO | WO-2015153507 A1 | 10/2015 |

OTHER PUBLICATIONS

"International Application Serial No. PCT/US2015/023410, International Search Report dated Jul. 7, 2015", 2 pgs.

"International Application Serial No. PCT/US2015/023410, Written Opinion dated Jul. 7, 2015", 6 pgs.

"International Application Serial No. PCT/US2015/023421, International Preliminary Report on Patentability dated Oct. 13, 2016", 8 pgs.

"International Application Serial No. PCT/US2015/023421, International Search Report dated Jul. 7, 2015", 2 pgs.

"International Application Serial No. PCT/US2015/023421, Written Opinion dated Jul. 7, 2015", 6 pgs.

\* cited by examiner

SIMULATED VALVE DEVICE FOR AIRWAY

INCORPORATION BY REFERENCE TO ANY PRIORITY APPLICATIONS

This Application claims from the benefit of U.S. Provisional Application Nos. 61/973,105, filed Mar. 31, 2014, titled "SIMULATED VALVE DEVICE FOR AIRWAY", 61/973,110, filed Mar. 31, 2014, titled "ENDOBRONCHIAL BRUSH DEVICE TO ESTIMATE SIZE OF AIRWAYS", 61/973,137, filed Mar. 31, 2014, titled "LIGHT-BASED ENDOLUMINAL SIZING DEVICE", 61/973,169, filed Mar. 31, 2014, titled "ENDOLUMINAL SIZING DEVICE", and 61/973,142, filed Mar. 31, 2014, titled "ANCHORING MECHANISMS AND SYSTEMS FOR ENDOLUMINAL DEVICES", the entirety of each of which is hereby incorporated by reference.

BACKGROUND

Field

The present disclosure generally relates to lung airway sizing devices using a simulated valve.

SUMMARY

Disclosed herein are embodiments of a simulated airway valve device comprising a shaft, and a simulated valve section comprising at least one radial strut extending generally radially from the shaft, at least one valve strut extending proximally and radially from the shaft and located proximal to the at least one radial strut, and a membrane at least partially covering the at least one radial strut and the at least one conical strut, wherein said simulated valve section, when disposed in an airway, is configured to approximate the size of an airway valve.

In some embodiments, the membrane can completely cover the at least one radial strut. In some embodiments, said sizing shaft can be at least partially disposable within a bronchoscope. In some embodiments, the device can further comprise at least one atraumatic anchor at the end of the at least one radial strut. In some embodiments, the simulated valve section can comprise a plurality of radial struts.

In some embodiments, the membrane can comprise at least one marker corresponding to a dimension of an airway. In some embodiments, the marker can comprise an annular marker. In some embodiments, the membrane can comprise plurality of markers, wherein the membrane is configured to contact an airway comprising a wall, such that the particular marker that contacts said airway wall indicates a dimension of said airway. In some embodiments, the membrane can permit airflow in a proximal direction past the simulated airway valve device and substantially occludes airflow in a distal direction past the simulated airway valve device when the simulated airway valve device is deployed in the airway and when the simulated airway valve device is of an appropriate size for the airway.

Also disclosed herein is an embodiment of a simulated airway valve device comprising a shaft and a generally tubular portion connected to the shaft and comprising a conical shaped portion, wherein a mouth of the conical shaped portion extends proximally, a radial shaped portion located distal from the conical shaped portion, and a membrane at least partially covering the conical and radial shaped portions, the membrane narrowing between the conical shaped portion and the radial shaped portion, wherein said generally tubular portion, when disposed in an airway, is configured to approximate the size of an airway valve.

Also disclosed herein are embodiments of a method of measuring an airway comprising inserting a bronchoscope into an airway of a patient, inserting a simulated valve section into said airway of said patient, wherein said simulated valve section comprises a plurality of struts and a membrane at least partially covering said struts, viewing at least part of said simulated valve section in said airway, and approximating a dimension of said airway based at least in part on whether said simulated valve section adequately seats within said airway.

In some embodiments, the method can further comprise inserting an airway valve sized similarly to said simulated valve section. In some embodiments, the method can further comprise inserting said simulated valve section into at least a portion of said bronchoscope. In some embodiments, viewing at least part of the said simulated valve section can comprise viewing the valving function of the simulated valve section in said airway.

In some embodiments, said membrane can substantially cover said struts. In some embodiments, said membrane can comprise at least one marker. In some embodiments, said marker can comprise an annular marker. In some embodiments, said marker can correspond to a dimension of said airway.

DETAILED DESCRIPTION

Disclosed herein are embodiments of devices that can be used for approximating the size of airways, specifically the size of the lumen of the airways to place a correctly sized valve. Advantageously, embodiments of the disclosed devices can include simulated valves which can be used to determining the proper size of a valve to be inserted into an airway and to test whether a particular valve would work properly in the airway.

If the airway is not adequately measured or approximated, this may result in an incorrect sized valve being implanted. Thus, the sizing preferably is done prior to the insertion of the valve in order to reduce the likelihood that an inappropriately-sized valve is used in an airway, thus inhibiting or preventing damage to the airway based on too large, or too small, of a valve. For example, too large of a valve for the diameter of an airway can lead to permanent rupturing or deformation of the airway.

Embodiments of the device can be used to size airways leading into a person's, or animal's, lungs for determination of the properly sized valve. However, the disclosed devices can be used to size other lumens as well, and the particular lumen being measuring is not limiting. Further, the measured dimensions can be, for example, volume, radius, or diameter, though the particular dimensions are not limiting.

Existing methods of sizing airways include balloons filled with a fluid, wherein the amount that the balloon is inflated, may correspond to the diameter of the airway. Other sizing devices may include tangs on a catheter. The flexible tangs may be of different heights away from the center of the catheter, and the operator may be able to determine if the airway is within a certain range of diameters. Other sizing devices may include an expanding triangle, wherein a catheter has a pull wire that when pulled back, expands two opposing members. When the members touch the wall, the diameter can be read off of the handle.

However, airways are not always round, but instead can be ovaloid, irregular, or other shapes. Additionally, airways are not always cylindrical, but instead may be frusto-conical, or maybe tapered to some degree.

Simulated Valve Device

Figure 1:
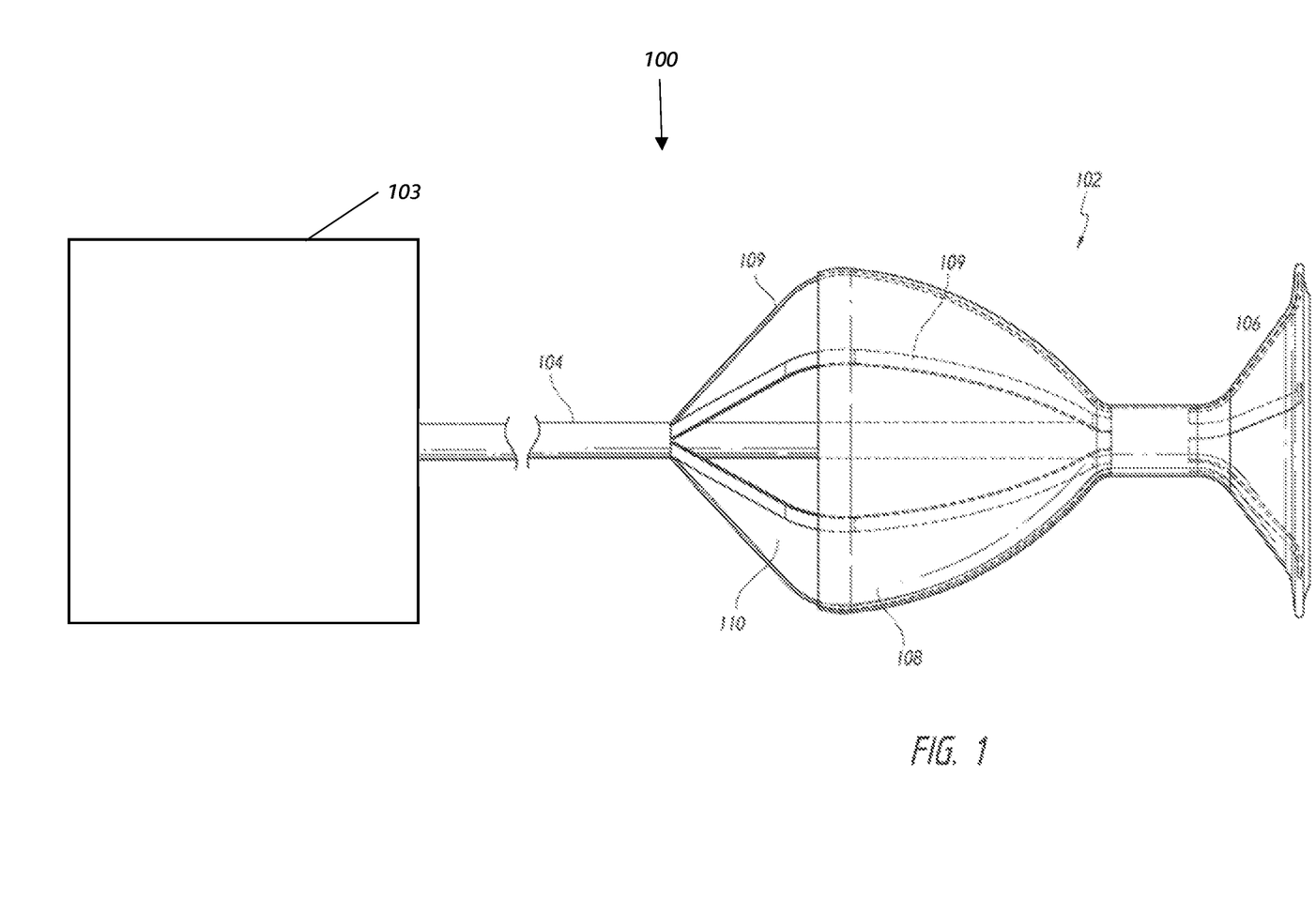
FIG. 1 shows an embodiment of a simulated valve device.

The disclosure and figures relate to the proximal end of a device having a simulated valve device. However, while not shown, in some embodiments the simulated valve device 100 can comprise at least a handle 103 at a proximal end for a user to manipulate, with the valve simulation mechanism at the distal end as shown in FIG. 1. The handle 103 may comprise a gripping portion, for which a user may grip or engage the airway sizing device, though the particular manipulation tool at the proximal end is not limiting, and different types of manipulation tools can be used.

Embodiments of the below disclosure can be advantageous for determining a particularly sized valve in a particular airway. In some embodiments of a simulated valve device, through the use of a simulated valve the device may be able to not only indicate the diameter or other dimension of the airway, as discussed below, but may indicate whether an implanted valve will function correctly. For example, a membrane feature may allow the user to determine if the valving action functions. The user may be able to see the membrane moving, or may see that there is a stop in airflow. The device may further comprise simulated anchors such that the user may be able to determine if the anchors of the final device will seat properly in the airway. The simulated anchors may be atraumatic, which may allow for easy removal.

In addition, embodiments of a simulated valve device may indicate whether an airway is round. Thus, even if the exact diameter or other dimension of the airway at or around the target site may not be precisely measured, the user may still be able to determine whether a valve of a specific size may be successfully implanted.

As shown in FIG. 1, the distal end of the simulated valve device may comprise a sizing mechanism, which may generally comprise a shaft 104 and a simulated valve section (e.g., flex section) 102. The shaft 104 can be flexible or stiff, and the particular stiffness of the shaft 104 is not limiting. In some embodiments, the shaft 104 can be a wire, or a plurality of wires. In some embodiments, the shaft 104 can connect to a wire, or plurality of wires, that extends to a proximal handle 103. In some embodiments, the shaft 104 can extend through the simulated valve section 102, though in some embodiments it only extends partially through the simulated valve section 102.

Figure 2:
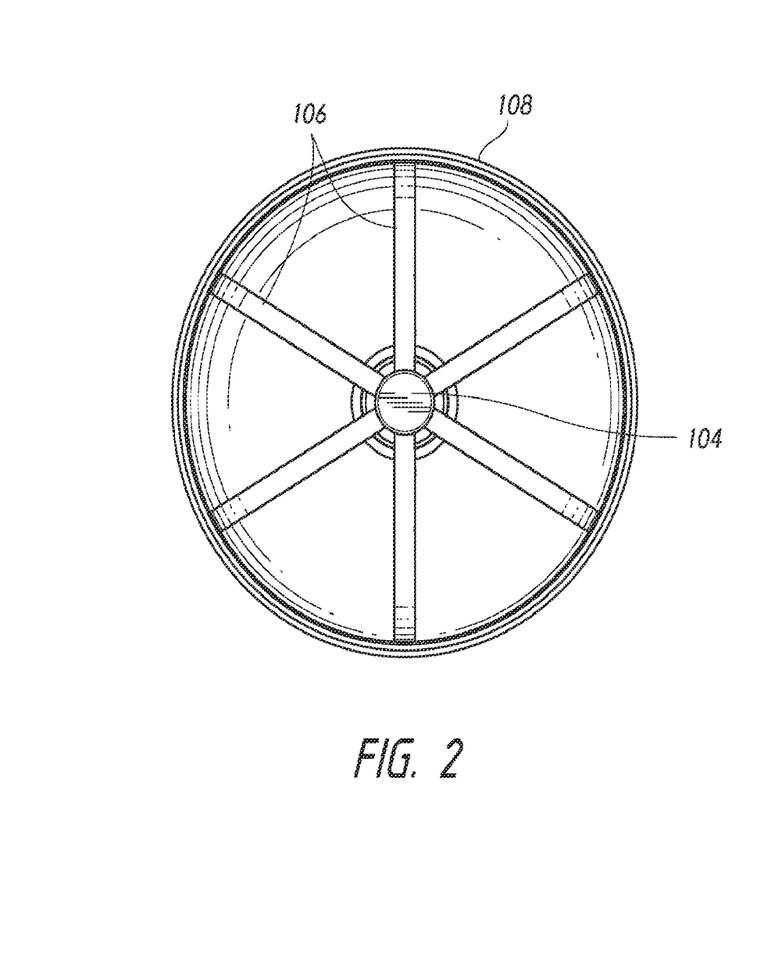
FIG. 2 shows a cross section of a simulated valve section of an embodiment of a simulated valve device.

The simulated valve section 102 may at least partially surround a portion of shaft 104. The simulated valve section 102 may correspond to one or more sizes of airway valves. For example, a user may operate the simulated valve section 102 at or around a target site in a patient's airway, to determine whether a particular sized valve may fit and/or be suitable for implantation in that portion of the airway. In some embodiments, the simulated valve section 102 can be contained within a sheath or catheter upon insertion into an airway, and can expand outwards upon removal of the sheath or catheter. In some embodiments, the simulated valve section 102 can be sized and configured similar to the valves described in U.S. Pat. Nos. 8,974,484, 6,929,637, 8,021,385, and 7,691,151, the entirety of each of which is hereby incorporated by reference. The simulated valve section 102 can perform As shown in FIG. 1, shaft 104 can be attached to one or more struts/anchors 106. In some embodiments, the shaft 104 and struts 106 can be made of a single piece of material. In some embodiments, the struts 106 can be attached to the shaft 104, for example by mechanical or chemical means though the attachment mechanism is not limiting. In some embodiments, the shaft 104 can be located generally at the center of the struts 106, which can extend radially outwards from the shaft 104 as shown in FIG. 2. The struts 106 may comprise Nitinol, or other biocompatible materials, which may be sufficiently elastic while disposed within the bronchoscope or within the patient's airway.

In some embodiments, at least part of the struts 106 may be covered and/or attached to a membrane 108. The membrane 108 may comprise a thin material, such as plastic, nylon, or other suitable material for use in the medical field. At least part of the simulated valve section 102 may comprise the membrane 108, and part of the simulated valve section 102 may not comprise the membrane 108, as shown as portion 110 in FIG. 1. For example, a proximal portion 110 of the simulated valve section 102 may not comprise a membrane 110, such that at least part of the simulated valve section 102 may resemble and generally act in a similar manner to an airway valve. In some embodiments, the simulated valve section 102 can be generally tubular, but be deformed based on the strut configuration discussed below, creating a configuration similar to that shown in FIG. 1.

For the portion covered by the membrane 108 extending proximally from the struts 106, a series valve struts 109 can extend in a generally conical or frusto-conical manner towards the distal end of the device, as shown in FIG. 1. Generally at the apex of the series valve struts 109, the membrane 108 may stop, and the series valve struts 109 may reduce in radius back towards the shaft 104. The series valve struts 109 may be integrally formed with the shaft 104 or may attach to the shaft 104 through, for example, chemical or mechanical means though the attachment is not limiting. Any number of valve struts 109 can be used, and the number of valve struts 109 is not limiting. Accordingly, the simulated valve section 102 can extend radially at two different points, e.g., at the struts 106 and at the valve struts 109. Thus, a deformed cylinder configuration similar to what is shown in FIG. 1 can be formed.

In some embodiments, the membrane 108 may extend completely around the distal end of the device, thus covering the struts 106. The membrane 108 at the distal end may be generally flat, or may have another configuration. In some embodiments, the membrane 108 may reduce in diameter moving towards the proximal end, and then may re-expand in diameter to cover the valve struts 109 as the membrane 108 follows along the path of the struts 106 and valve struts 109. As shown in FIG. 1, the membrane 108 around the struts 106 may increase and decrease in radius in a short distance, whereas the membrane 108 around the valve struts 109 may increase in radius in a longer fashion. In some embodiments, the radius of the membrane 108 around the struts 106 and around the valve struts 109 may be approximately the same. In some embodiments, the radius of the membrane 108 around the struts 106 may be greater than the radius around the valve struts 109. In some embodiments, the radius of the membrane 108 around the struts 106 may be less than the radius around the valve struts 109. In some embodiments, the membrane 108 may be formed by dipping the device into a material that solidifies onto the device.

As shown in FIG. 2, cross sectional view of the simulated valve section 102 viewed towards the distal end of the device, the shaft 104 may be disposed in the middle of the simulated valve section 102. There may be 1, 2, 3, 4, 5, 6, 7, 8, 9, or 10 struts 106 extending from the shaft 104, though the number of struts 106 is not limiting. In some embodiments, the radial ends of the struts 106 may be generally rounded so as not to pierce or damage the membrane 108 which can surround the struts 106. In some embodiments, the struts 106 may have an anchoring shape on their distal ends. In some embodiments, the anchoring shape may cause the membrane 108 for form an anchoring shape as well. In some embodiments, the struts 106 may be generally flat at the radial end, and the particular shape of the struts 106 is not limiting. In some embodiments, all of the struts 106 may have the same length. In some embodiments, the struts 106 may have different lengths. In some embodiments, struts 106 directly opposite on the shaft 104 may have the same length, but other pairs of struts 106 may have different lengths.

Figure 3:
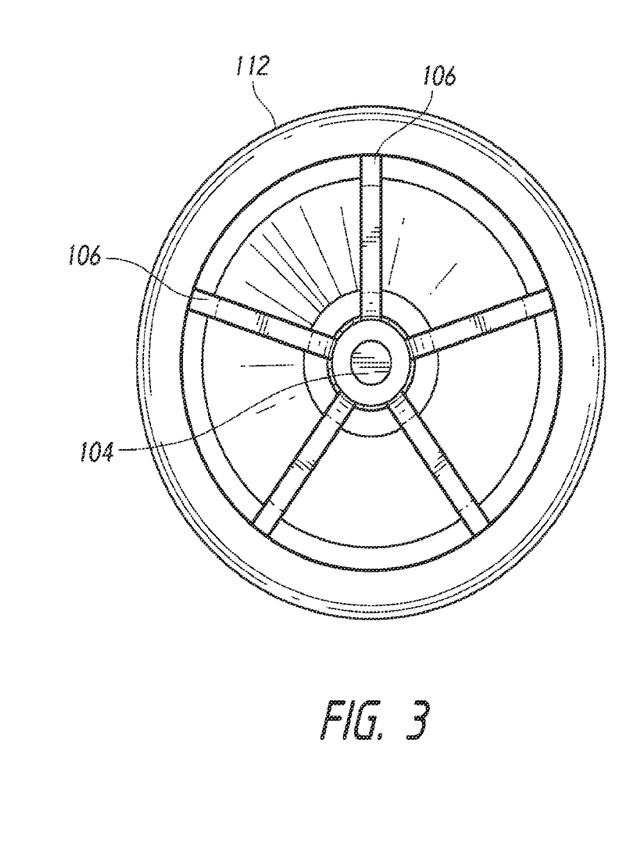
FIG. 3 shows a cross section of an embodiment of a simulated valve device.

The struts 106 may extend outward and engage the membrane 108, and the membrane 108 may overlay the struts 106. The membrane 108 may encompass at least some of, and in some embodiments all of, the struts 106. In some embodiments, the membrane 108 may form a generally circular cross section, such as shown in FIG. 2. In some embodiments, the membrane 108 may curve radially inwards between struts 106, thereby forming an umbrella configuration. In FIG. 2, the spaces between each strut may represent the inside surface of the membrane 108. For example, the membrane 108 may encompass the outermost portion of the struts 106 and then taper towards the distal end of the simulated valve section 102. As shown in FIG. 3, the struts 106 may extend from the center of the simulated valve section 102, such that the ends of the struts 106 may contact the walls 112 of the airway.

In some embodiments, one simulated valve section 102 may correspond to a single size of an airway valve. For example, when embodiments of the simulated valve device is placed within a patient's airway, and the valve device adequately fits within the patient's airway at or around the target site, this may indicate whether a similarly sized valve would also adequately fit within the patient's airway at or around the target site, and be suitable for implantation. If the valve device is too large for the patient's airway at or around the target site, the user may decide to replace the simulated valve device with the one that is of a smaller size, and repeat the sizing process. If the valve device is too small for the patient's airway at or around the target site, the user may decide to replace the simulated valve device with one that is of a larger size, and repeat the sizing process. This process is further discussed below.

Additionally, in some embodiments, at least part of the airway sizing device may be configured to be used and/or disposable within a working channel or lumen of a bronchoscope, though other equipment can be used as well. A bronchoscope may comprise an aperture for an electronic device, which may comprise a camera or a plurality of cameras. The aperture for the camera may be adjacent the aperture for the shaft. The camera may be disposed outside of the aperture or within the aperture or proximal the aperture. The camera may be in operational communication with a viewing device, such that a user of the bronchoscope or the simulated valve device may observe visual images based on the information transmitted by the camera.

Figure 4A:
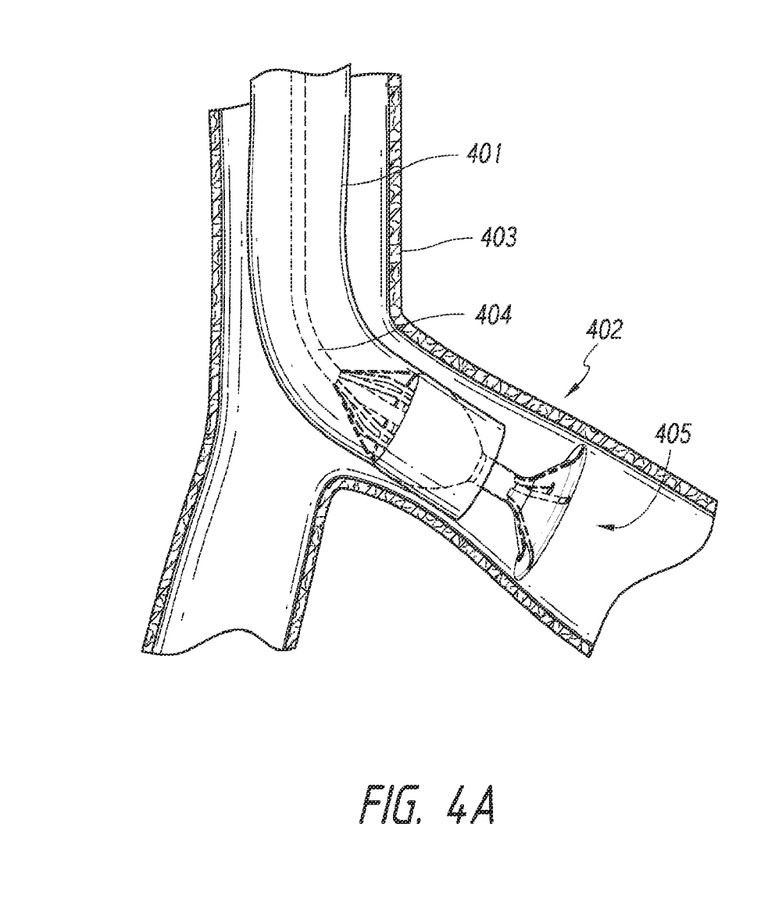
FIGS. 4A-B shows a use of an embodiment of a simulated valve device in an airway.
Figure 4B:
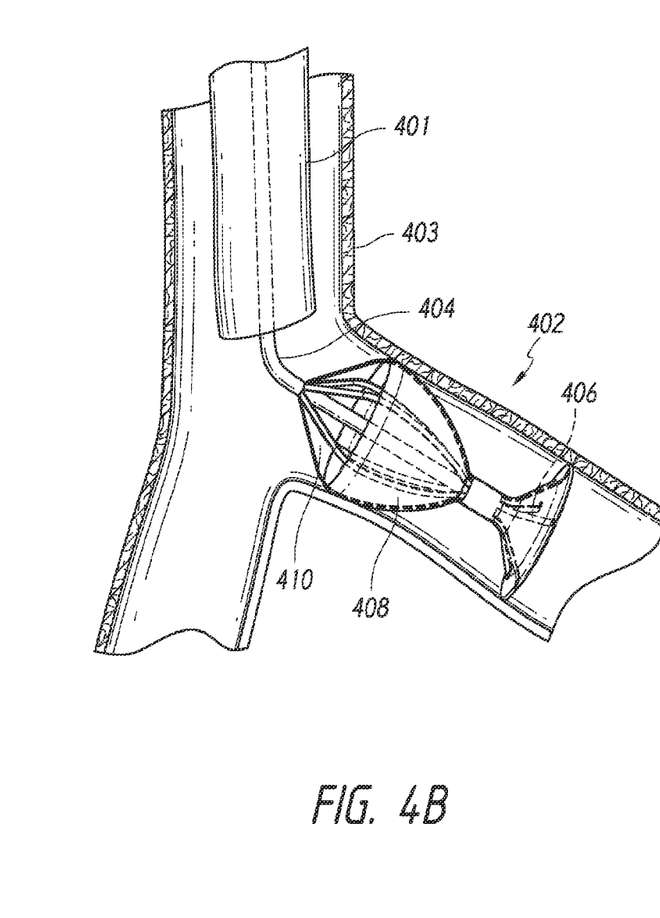

As shown in FIGS. 4A and 4B, to use the simulated valve device 402, a user may insert the distal end 405 into the patient's airway 403 and direct it down the airway (such as leading to a lung) 403 as would be known by those skilled in the art. The simulated valve section 402 may be positioned/located in the airway 403 desired by the user at or around the target airway 403. Similar and/or identical to the device described in detail above, the device 402 may have a shaft 404, struts 406, a membrane 408 and a non-membrane portion 410.

At least part of the device may be evaluated through an electronic device such as a camera lens that may be disposed at the distal end of the bronchoscope 401. This may inform the user whether an airway valve that is sized similarly to the simulated valve device may adequately fit within the patient's airway 403 at the target site. Further, the user may perform tests on the patient with the simulated valve section in situ 402 to determine if a valve would be operational at the current location. If the simulated valve device does adequately fit in the patient's airway 403 at the target site, then the user may remove the device, and may proceed to implant a valve in the airway 403 at or around the target site.

If the simulated valve device does not adequately fit within the patient's airway 403 at the target site, the user may decide from at least two options. First, the user may remove the sizing device and replace it with a different sized sizing device, wherein the new sizing device may correspond to a different sized airway valve. Or the user may move the sizing device to a different location along the airway 403, until a location that matches the desired valve size is found.

Figure 5:
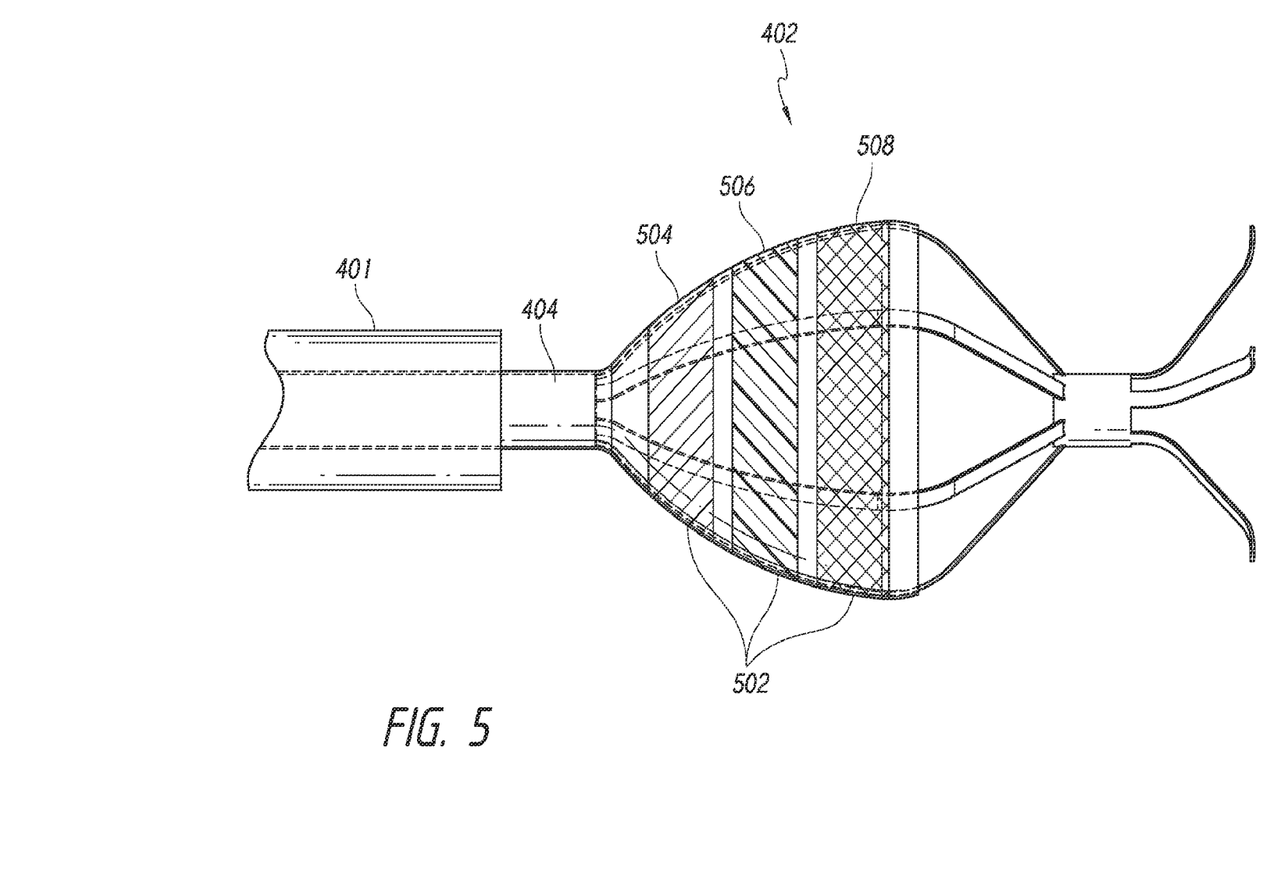
FIG. 5 shows an embodiment of a simulated valve device having sizing markings.

As shown in FIG. 5, in some embodiments, the simulated valve section 402 may comprise one or more portions 504/506/508 along the valve struts (109 in FIG. 1) which are not covered by membrane 108, shown as section 110, wherein at least part of the simulated valve section 402 may comprise a marker or marking that may indicate the size or diameter of the patient's airway at or around the target site. In some embodiments, a membrane 502 may be used which can cover section 110 with the markings. In some embodiments, the membrane 502 may be membrane 408, or an extension of membrane 408. While membrane 408 is not shown in FIG. 5, in some embodiments membrane 408 can cover the distal portion of the device as discussed in detail above. In some embodiments, membranes 408/502 can contact one another to form a continuous surface. In some embodiments, membranes 408/502 can be the same membrane. In some embodiments, the markings may be annular rings or bands that are retained onto the valve struts 109 in the uncovered section 110. In some embodiments, the markers can be annular. In some embodiments, the markers may be partially annular. Markers may comprise patterns, colors, textures, fluorescence, or other features. For instance, the simulated valve section 402 may comprise a first band 504 that radially extends around the simulated valve section 402, which can comprise a marker, such that when the simulated valve section 402 is disposed within an airway, at least part of the first band 504 engages the wall of the airway. The markers may be on the struts 106, valve struts 109, or membrane 108, and the positioning of the markers is not limiting.

The first band 504 may correspond to a specific diameter or radius, which may be 5 mm as an example. The simulated valve section 402 may further comprise a second band 506, which may correspond to a specific diameter or radius, which may be 6 mm as an example. The simulated valve section 402 may further comprise a third band 508, which may correspond to a specific diameter or radius, which may be 7 mm as an example. The third band 508 may be disposed on a portion of the simulated valve section 402 that has a larger diameter than the portion of the simulated valve section 402 on which the first band is disposed. Thus, when the simulated valve section 402 is inserted into the patient's airway and disposed at or around the target site, the diameter or size of the airway may be approximated by the user based on which of the first 504, second 506, or third band 508, engage/touch/interact with the wall of the airway. While the above discloses different diameter or radius, different diameters or radii may be used and the particular dimensions of the bands is not limiting to the disclosure.

Figure 6:
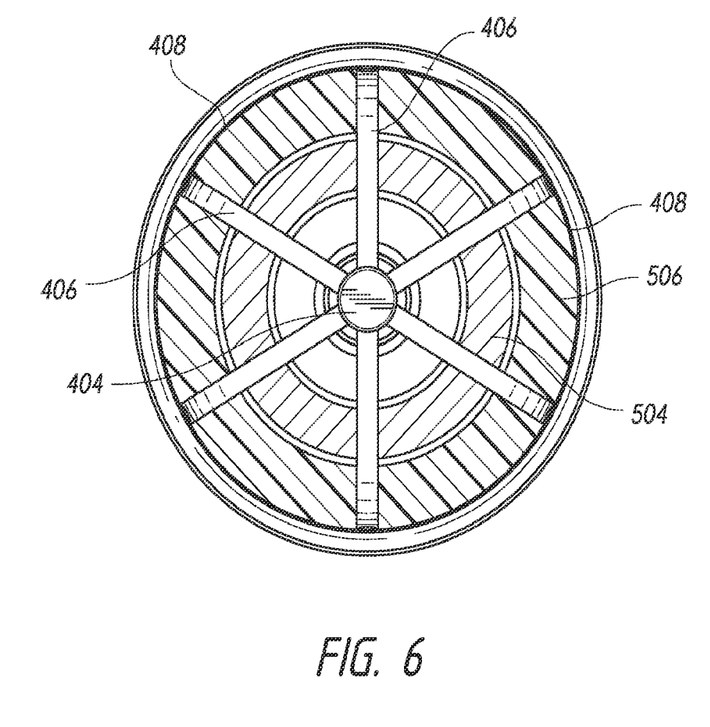
FIG. 6 shows a cross section of an embodiment of a simulated valve device having sizing markings.

For instance, as shown in FIG. 6, the 5 mm band 504 does not engage the walls of the airway, but at least part of the 6 mm band 506 is shown as engaging the airway. Thus, a 5 mm valve may be too small for the airway where it was measured, but a 6 mm valve may be a more appropriate size.

In some embodiments, the device may comprise an aspirator, which may be used to remove mucus or other substances, in order that the device may make better contact with the airway walls. In addition, removing mucus or other substances may allow for better visualization of the device engaging the airway or the airway walls at or around the target site.

In some embodiments, a stop could be located at the distal end of the device. The stop could then be pulled proximally, which would collapse the device and assist the retrieval of the device. For example, pulling on the stop could collapse the device into a sheath or catheter for ease of retrieval.

From the foregoing description, it will be appreciated that an inventive airway lumen sizing device is disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations and/or "some embodiments" can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X. Y, or Z. Thus, such conjunctive language is not generally intended to imply that certain embodiments require the presence of at least one of X, at least one of Y, and at least one of Z.

Language of degree used herein, such as the terms "approximately," "about," "generally." and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A simulated airway valve device comprising:
    a handle;
    a shaft configured to extend from the handle; and
    a simulated valve section comprising:
        at least one anchor strut including a first end extending generally radially from the shaft;
        at least one valve strut extending proximally and radially from the shaft and located proximal to the at least one anchor strut, wherein the at least one valve strut includes a simulated valve portion and a proximal portion; and a membrane including a first membrane portion covering radial ends of the at least one anchor strut and a second membrane portion partially covering the at least one valve strut,
  wherein the membrane reduces in diameter moving proximally from a distal end of the first membrane portion and then the second membrane portion expands in diameter moving proximally to partially cover the at least one valve strut;
  wherein the simulated valve section, when disposed in an airway, is configured to approximate the size of an airway valve,
  wherein the proximal portion of the at least one valve strut that is at least partially covered by the second membrane portion is directly connected to the shaft,
  wherein a proximal end of the membrane is located at a transition between the proximal portion and the simulated valve portion of the at least one valve strut,
  wherein the proximal end of the at least one valve strut is not a free end,
  wherein the at least one anchor strut is located distal from the at least one valve strut.

2. The device of claim 1, wherein the membrane completely covers the at least one anchor strut.

3. The device of claim 1, wherein the shaft is at least partially disposable within a bronchoscope.

4. The device of claim 1, further comprising at least one atraumatic anchor at the end of the at least one anchor strut.

5. The device of claim 1, wherein the simulated valve section comprises a plurality of anchor struts.

6. The device of claim 1, wherein the membrane permits airflow in a proximal direction past the simulated airway valve device and substantially occludes airflow in a distal direction past the simulated airway valve device when the simulated airway valve device is deployed in the airway and when the simulated airway valve device is of an appropriate size for the airway.

7. The device of claim 2, wherein the membrane fully covers the simulated valve portion of the at least one valve strut.

8. The device of claim 1, wherein the at least one anchor strut includes an unattached second end.

9. A simulated airway valve device comprising:
a handle;
a shaft configured to extend from the handle;
a simulated anchor section comprising:
  at least one anchor strut including a first end configured to extend radially from a distal end of the shaft; and
  a first membrane extending completely around a distal end of the simulated airway device and covering the at least one anchor strut; and
a simulated valve section comprising:
  at least one strut extending proximally and radially from a first section of the shaft and extending distally and radially from a second section of the shaft, wherein a distal portion of the at least one strut is a simulated valve portion; and
  a second membrane covering the distal portion of the simulated valve section up to an apex of the at least one strut, wherein the second membrane expands in diameter moving proximally up to the apex;
  wherein the first section of the shaft is distal of the second section of the shaft and proximal of the simulated anchor section;
  wherein the at least one anchor strut is located distal from the at least one strut.

10. The device of claim 9, wherein the at least one anchor strut includes an unattached second end.

11. The device of claim 1, wherein the second membrane portion includes markings configured to indicate a size or a diameter of a patient's airway.

12. The device of claim 11, wherein the markings include annular rings.

13. The device of claim 11, wherein the markings include patterns, colors, textures, or fluorescence.

14. The device of claim 9, wherein the second membrane includes markings configured to indicate a size or a diameter of a patient's airway.

15. The device of claim 14, wherein the markings include annular rings.

16. The device of claim 14, wherein the markings include patterns, colors, textures, or fluorescence.

* * * * *